(12) United States Patent
Ho et al.

(10) Patent No.: US 7,296,574 B2
(45) Date of Patent: Nov. 20, 2007

(54) FOREHEAD PAD AND FOREHEAD SUPPORT USING SAME

(75) Inventors: Peter Ho, Pittsburg, PA (US); Lance Busch, Trafford, PA (US)

(73) Assignee: RIC Investments, LLC, Wilmington, DE (US)

(*) Notice: Subject to any disclaimer, the term of this patent is extended or adjusted under 35 U.S.C. 154(b) by 106 days.

(21) Appl. No.: 10/884,060

(22) Filed: Jul. 2, 2004

(65) Prior Publication Data
US 2005/0011522 A1 Jan. 20, 2005

Related U.S. Application Data

(60) Provisional application No. 60/488,474, filed on Jul. 18, 2003.

(51) Int. Cl.
*A61M 16/06* (2006.01)
(52) U.S. Cl. .................. 128/207.11; 128/201.24; 128/207.13; 128/207.17; 128/207.18
(58) Field of Classification Search ........ 128/207.11, 128/206.27, 207.17, 202.27, 203.28, 204.11, 128/206.23, 201.24, 207.13, 207.18; 5/636–645; 297/391–410; 2/424, 417
See application file for complete search history.

(56) References Cited

U.S. PATENT DOCUMENTS

| | | | |
|---|---|---|---|
| 3,362,403 A * | 1/1968 | Fleming et al. ........ | 128/201.24 |
| 3,622,233 A * | 11/1971 | Blood et al. ................. | 351/245 |
| 4,907,584 A | 3/1990 | McGinnis | |
| 5,243,971 A | 9/1993 | Sullivan et al. | |
| 5,517,986 A | 5/1996 | Starr et al. | |
| 5,570,689 A | 11/1996 | Starr et al. | |
| 6,119,693 A | 9/2000 | Kwok et al. | |
| D439,326 S * | 3/2001 | Hecker et al. .......... | D24/110.5 |
| 6,357,441 B1 | 3/2002 | Kwok et al. | |
| 6,463,931 B1 * | 10/2002 | Kwok et al. ........... | 128/207.11 |
| 6,467,483 B1 | 10/2002 | Kopacko et al. | |
| 6,520,182 B1 * | 2/2003 | Gunaratnam ........... | 128/206.27 |
| 6,532,961 B1 | 3/2003 | Kwok et al. | |
| 6,557,556 B2 | 5/2003 | Kwok et al. | |
| 6,679,261 B2 * | 1/2004 | Lithgow et al. ........ | 128/207.11 |
| 2004/0112387 A1 * | 6/2004 | Lang et al. ............ | 128/206.24 |
| 2005/0022820 A1 * | 2/2005 | Kwok et al. ........... | 128/206.21 |

OTHER PUBLICATIONS

MAP Medizin-Technologie GmbH, Papillon® Instruction Manual, 2002.
MAP Medizin-Technologie GmbH, Papillon® Instruction Manual.
Respironics, Inc., ComfortClassic™, 2001.

* cited by examiner

*Primary Examiner*—Justine R. Yu
*Assistant Examiner*—Shumaya Ali
(74) *Attorney, Agent, or Firm*—Michael W. Haas (57) ABSTRACT

A forehead pad that includes a base member having a first side adapted to be coupled to a forehead support member. The pad also includes a patient contacting member having a first side adapted to contact a surface of a patient. A neck portion couples a second side of the base member and a second side of the first patient contacting member. The neck portion includes at least one cutout to allow at least a portion of the first patient contacting member to move relative to the base member so that the patient contacting portion of the pad is self-aligning with the surface of the patient even if the base member is not parallel with the surface of the patient.

18 Claims, 10 Drawing Sheets

FOREHEAD PAD AND FOREHEAD SUPPORT USING SAME

CROSS-REFERENCE TO RELATED APPLICATIONS

This application claims priority under 35 U.S.C. § 119(e) from provisional U.S. patent application No. 60/488,474 filed Jul. 18, 2003 the contents of which are incorporated herein by reference.

BACKGROUND OF THE INVENTION

1. Field of the Invention

The present invention pertains to a forehead pad and forehead support pad for use in a forehead support portion of a patient interface device, such as a nasal or full face mask.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle or with the condition of the patient (auto-titration pressure support systems), to treat a medical disorder, such as sleep apnea syndrome, in particular, obstructive sleep apnea (OSA) or congestive heart failure.

Non-invasive ventilation and pressure support therapies involve the placement of a patient interface device, which is typically a nasal or nasal/oral mask, on the face of a patient to interface the ventilator or pressure support device with the airway of the patient so that a flow of breathing gas can be delivered from the pressure/flow generating device to the airway of the patient. Because such masks are typically worn for an extended period of time, it is important the mask fit properly and comfortably on the patient. This is made difficult in that in order for the mask to maintain a seal without any undue gas leaks around the periphery of the mask, the mask may be compressed against the patient's face.

It is known to provide forehead supports associated with gas delivery masks to provide a support mechanism between the mask and the patient's forehead. Gas delivery masks having forehead cushions, spacers or supports are described in U.S. Pat. Nos. 4,907,584; 5,243,971; 5,570,689; 6,119,693; 6,357,441; 6,463,931; 6,467,483; 6,520,182; 6,532,961; 6,557,556. The forehead supports prevent the mask from exerting too much force on a patient's face and provides stability to the mask.

The forehead support devices in the above-identified patents typically have at least one forehead pad attached to the forehead support. The forehead pad contacts the surface of the patient. In U.S. Pat. Nos. 4,907,584; 5,243,971; 5,517,986, 5,570,689, and 6,357,441 the forehead support pads typically made of foam and have a generally rectangular or trapezoidal in shape with relatively sharp edges. The conventional forehead pads taught in U.S. Pat. Nos. 6,119,693; 6,463,931; 6,467,483; 6,520,182; 6,532,961; and 6,557,556 have a semi-circular profile to compensate for any angular variation between the forehead support structure and the surface of the patient. The disadvantage of that is the pad rests on the forehead on a curved surface which translates into pressure point. These semi-circular designs allow the curved contact to compress and deform to secure a flatter contact. Again, that creates pressure points and it is not the most comfortable option.

The product literature for the MAP Papillon mask shows a forehead pad that attaches to the forehead support via a stem. The stem and/or the attachment of the stem to the forehead support frame allows for some articulation of the main portion of the forehead pad. However, the relatively small size of the stem provides a relatively unstable platform for mounting the forehead pad on the support frame.

SUMMARY OF THE INVENTION

Accordingly, it is an object of the present invention to provide a forehead pad that overcomes the shortcomings of conventional forehead pads. This object is achieved according to one embodiment of the present invention by providing a forehead pad that includes a base member having a first side adapted to be coupled to a forehead support member and a second side. The forehead pad also includes a patient contacting member having a first side adapted to contact a surface of a patient and a second side. A neck portion is coupled to the second side of the base member and the second side of the patient contacting member to join these to portions of the forehead pad. The neck portion includes at least one cutout to allow at least a portion of the patient contacting member to move relative to the base member. This configuration allows the patient contacting member to automatically adjust relative to the base member so as to allow the first side of the patient contacting member to lie flat on the surface of the patient even if the base member is not parallel to the surface of the patient.

It is yet another object of the present invention to provide a forehead support assembly including the forehead support pad of the present invention.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

FIGS. 1-3C illustrates a first exemplary embodiment of a forehead pad 30 according to the principles of the present invention. Forehead pad 30 includes a base member 32 having a first side 34 adapted to be coupled to a forehead support member and a second side 36. Forehead pad 30 also includes a patient contacting member 38 having a first side 40 adapted to contact a surface of a patient and a second side 42. A neck portion 44 couples second side 36 of base member 32 and second side 42 patient-contacting member 38. In a preferred embodiment of the present invention, the base member, patient contacting member and neck portion are integrally formed from a common material, such as a low-durometer silicone or soft elastomer.

Neck portion 44, base member 32, and patient contacting member 38 are configured such that a cutout, generally indicated at 46a and 46b, is provided on each side of the forehead pad. Cutouts 46a and 46b allow at least a portion of patient contacting member 38 to move relative to base member 32, as indicated by arrow A. In other words, a cantilever member 48a and 48b is formed on each side of patient contacting member 38. Cantilever members 48a and 48b are deflectable toward base member 32 as a compression force is applied to first side 40 of patient contacting member 38.

The flexibility of the material defining the patient contacting member and the neck portion as well as the cutout portions at the neck region allows patient contacting surface 40 to rock up-and-down, as indicated by arrow A, when the forehead pad is compressed. Cutouts 46a and 46b also absorb the force acting on the forehead. Thus, the forehead pad of the present invention ensures a flat contact that provides optimal comfort to the patent regardless of the angle at which the overall forehead pad contacts the patient. In other words, any angle between the base member and the surface of the patient is adjusted for by allowing the patient contacting member to change position relative to the base member. As a result, the surface of the forehead pad contacting the patient evenly distributes the loading to eliminate pressure points. In addition, this configuration of the forehead pad allows the pad to self align with the forehead so it will always maintain a flat surface contact.

In the illustrated embodiment cutouts 46a and 46b are sized and configured such that an angle α of approximately 30 degrees is defined between second 36 side of base member 32 and second side 42 of the patient contacting member 38. It is to be understood that other angles are possible depending on the freedom of movement desired for the patient contacting member. In addition, cutouts 46a and 46b are shown as being symmetrically disposed on each side of the forehead pad. It is to be understood that either of these cutouts can be eliminated so that only one cutout is provided. Of course, this configuration will limit the degree of movement for the patient contacting member.

It is to be further understood that other cutout arrangements can be provided to allow movement of patient contacting member 38 relative to base member 32 in other dimensions. For example, the present invention contemplates providing cutouts 47a and 47b on the sides of the pad, and not just on the front and back portions. Thus, additional cantilevered members 49a and 49b are formed from patient contacting portion due to side cutouts 47a and 47b.

In the illustrated exemplary embodiment, first side 40 of patient contacting member 38 is relatively planar, i.e., relatively flat. It is to be understood, however, that other configurations for the patient contacting member and patient contacting surface 40 of the present invention are contemplated by this invention. For example, first side 40 can be provided with a slight concavity to account for the slight rounding present in the forehead of many humans.

Figure 1:
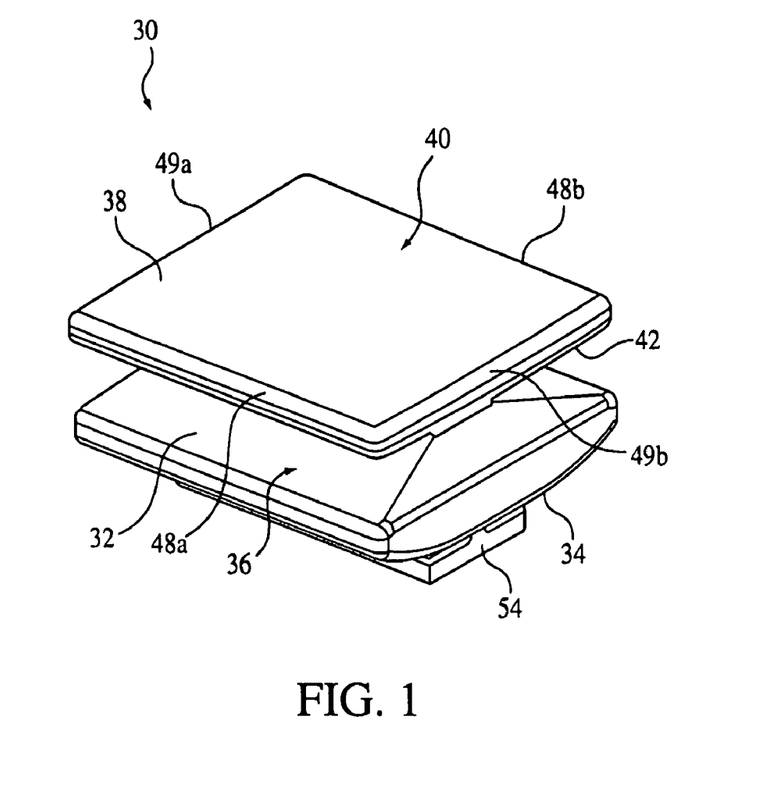
FIG. 1 is a top perspective view of a first embodiment of a forehead pad according to the principles of the present invention.
Figure 2:
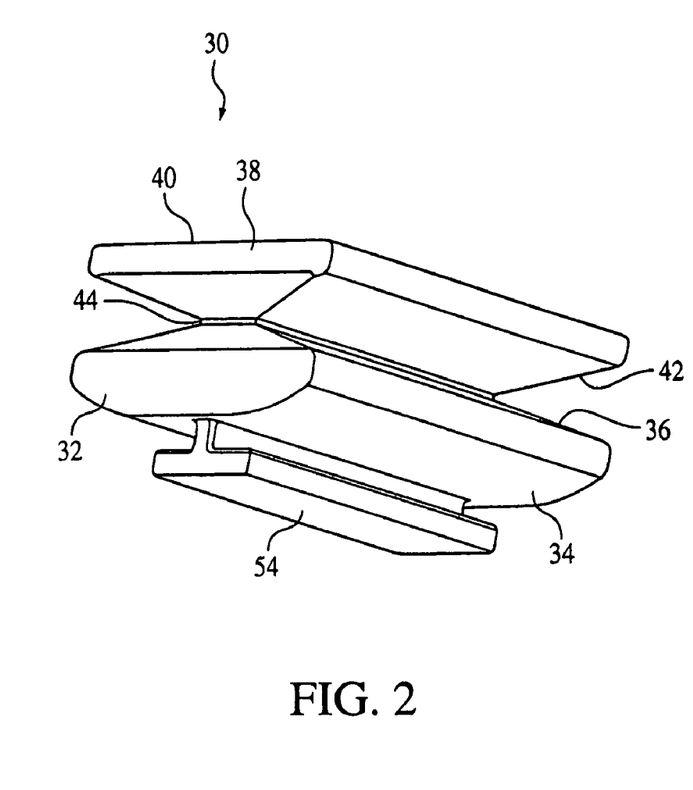
FIG. 2 is a bottom perspective view of the forehead pad of FIG. 1.
Figure 3A:
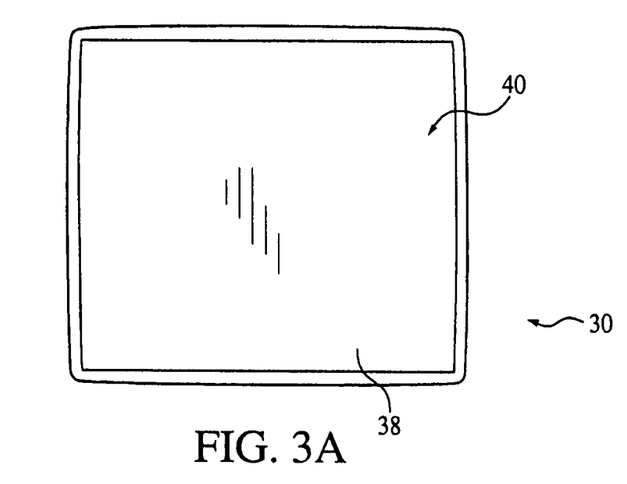
FIGS. 3A, 3B, and 3C are top, front, and side views, respectively, of the forehead pad of FIG. 1.
Figure 3B:
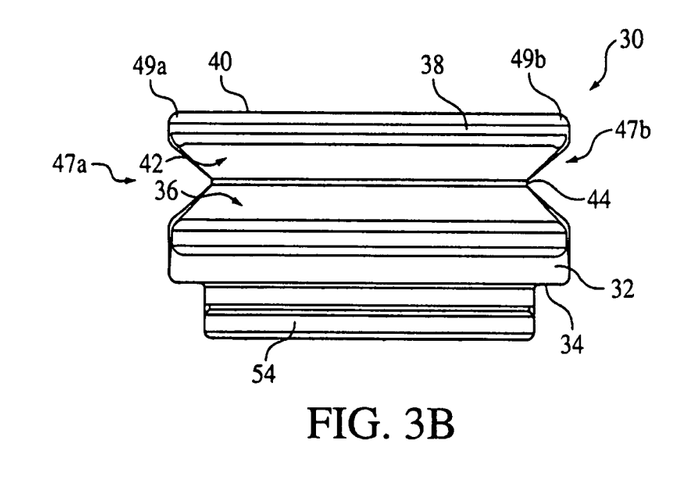
Figure 3C:
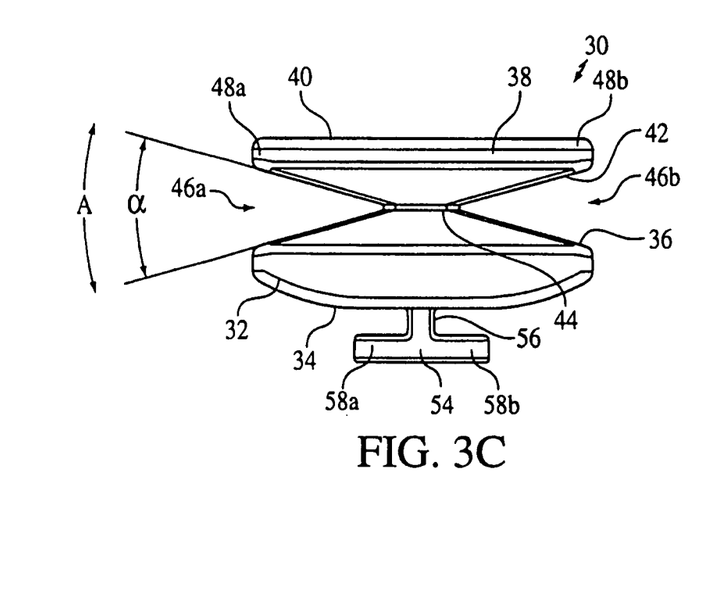
Figure 4:
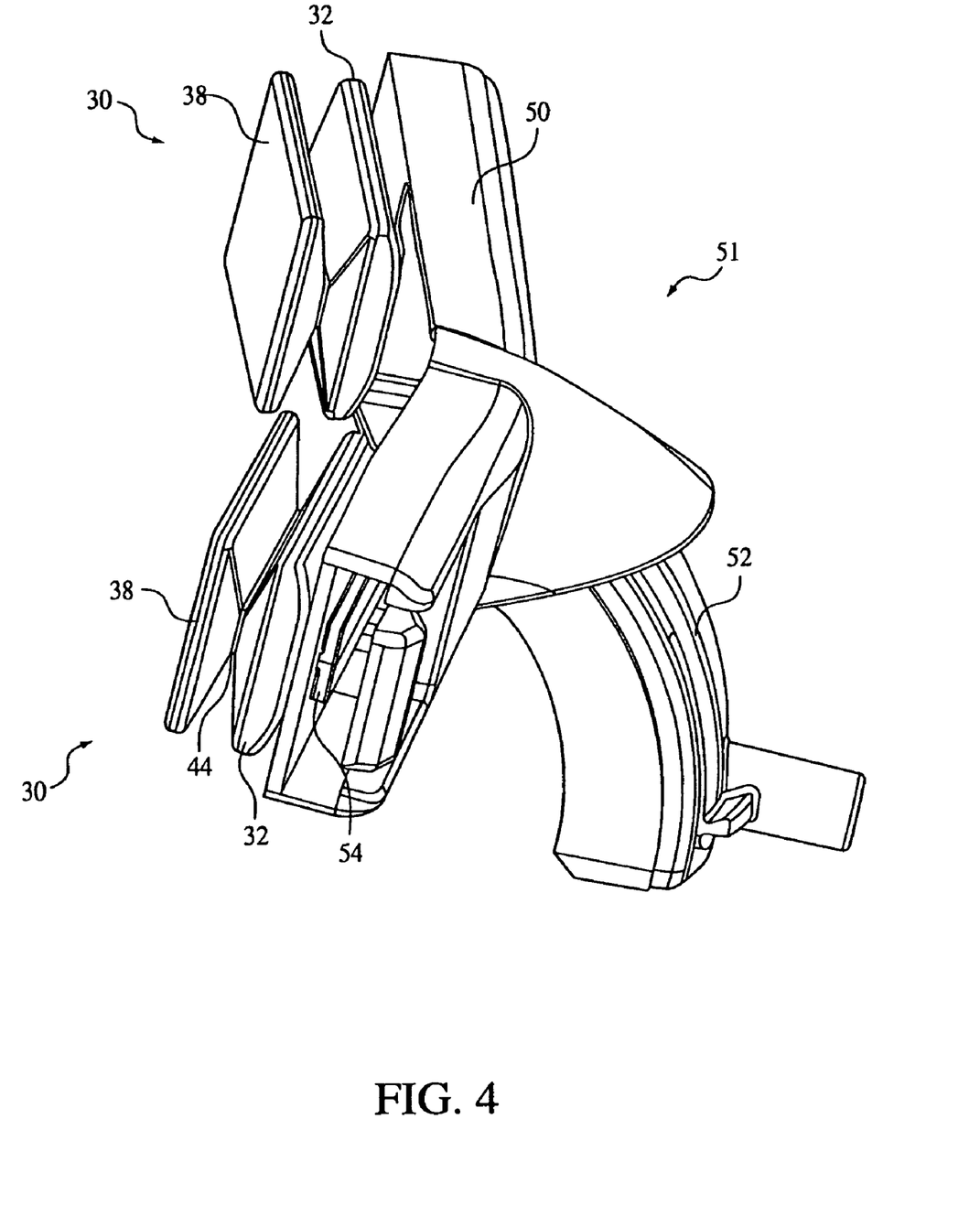
FIG. 4 is a top perspective view showing the forehead pad of FIG. 1 attached to a first embodiment of a forehead support member according to the principles of the present invention.
Figure 5A:
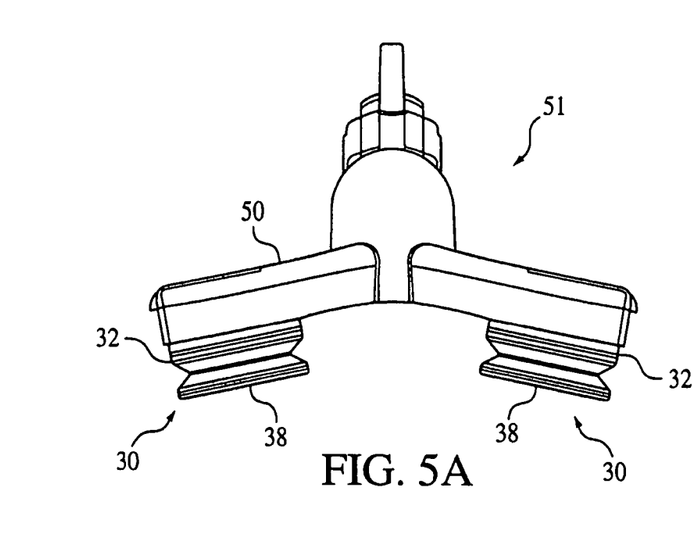
FIGS. 5A, 5B, and 5C are top, front, and side views, respectively, of the forehead pad and forehead support combination of FIG. 4.
Figure 5B:
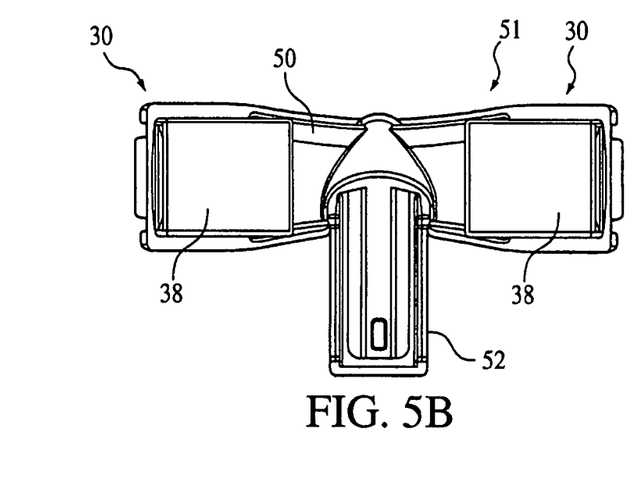
Figure 5C:
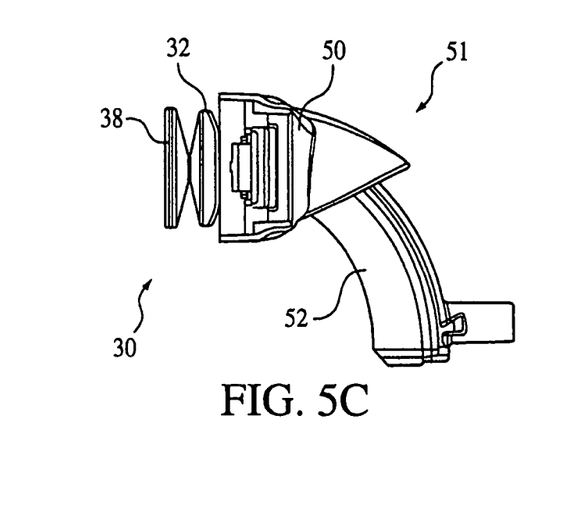
Figure 6:
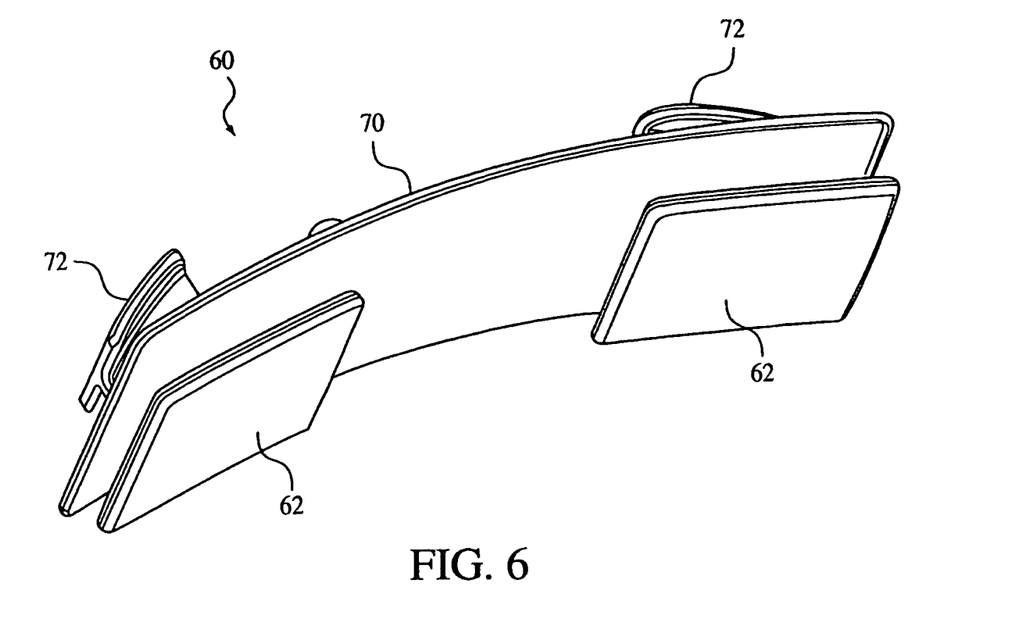
FIG. 6 is a top perspective view of a second embodiment of a forehead pad according to the principles of the present invention.
Figure 7:
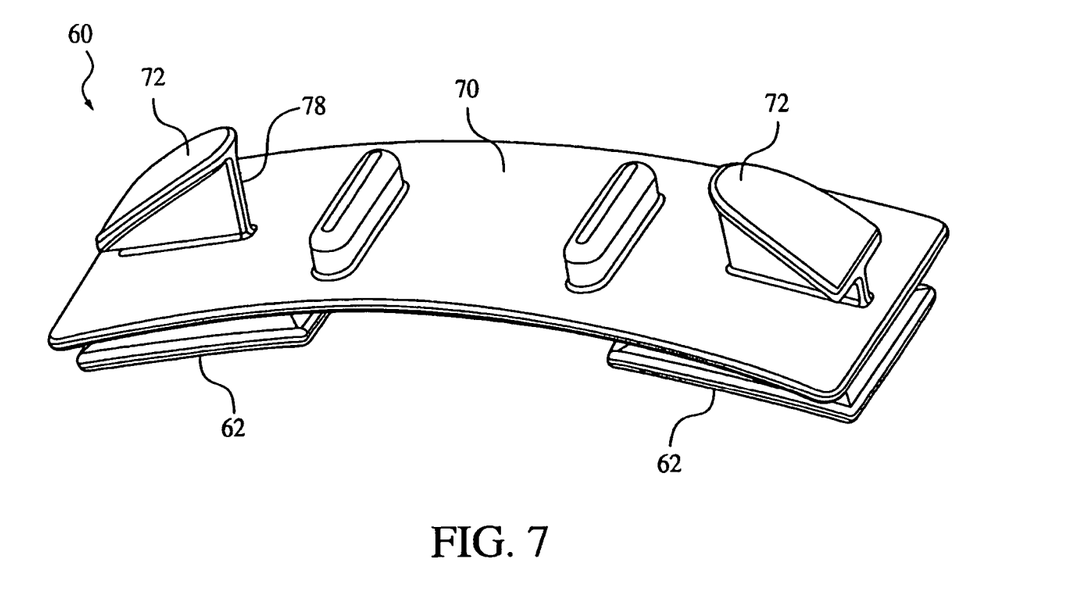
FIG. 7 is a bottom perspective view of the forehead pad of FIG. 6.
Figure 8A:
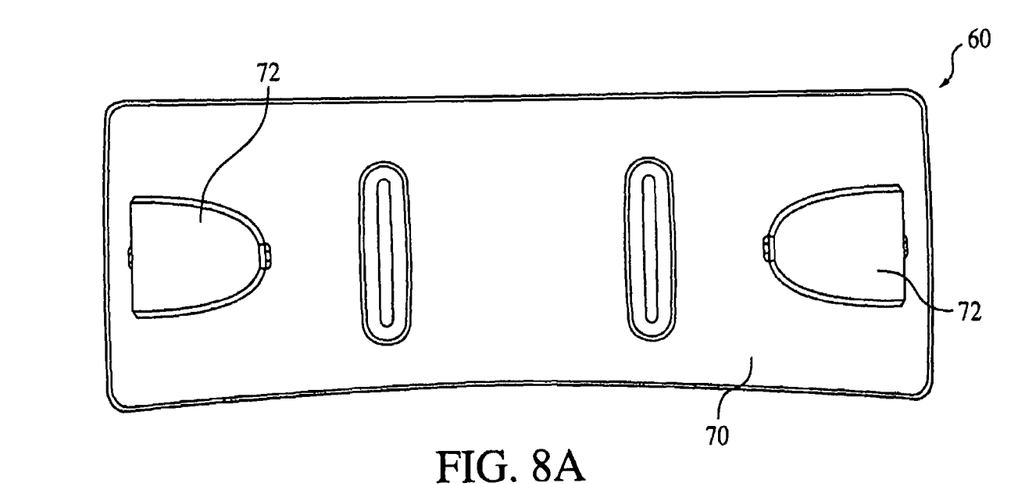
FIGS. 8A, 8B, and 8C are top, front, and side views, respectively, of the forehead pad of FIG. 6.
Figure 8B:
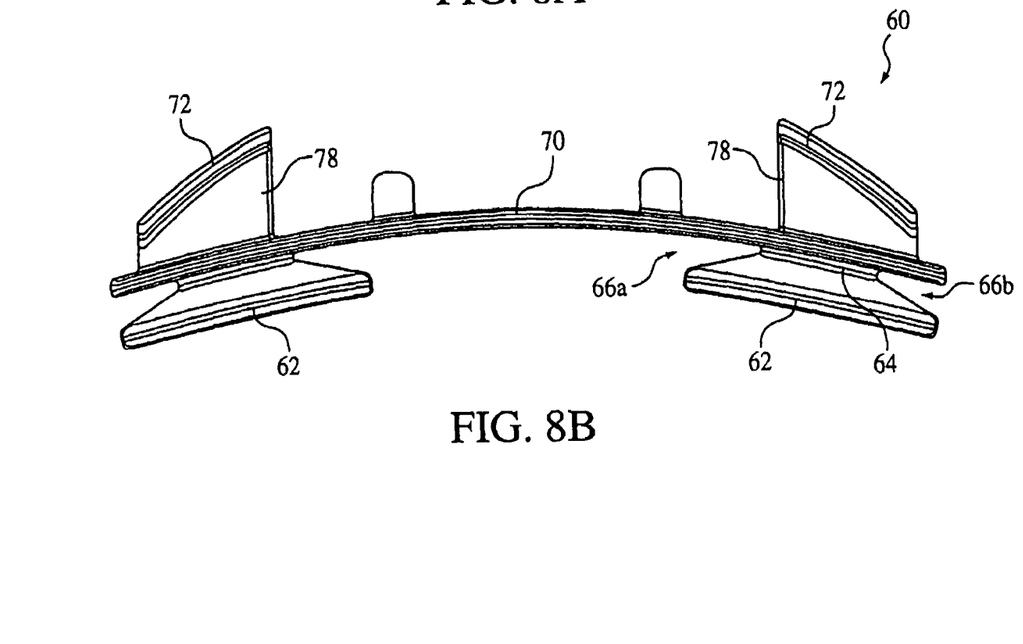
Figure 8C:
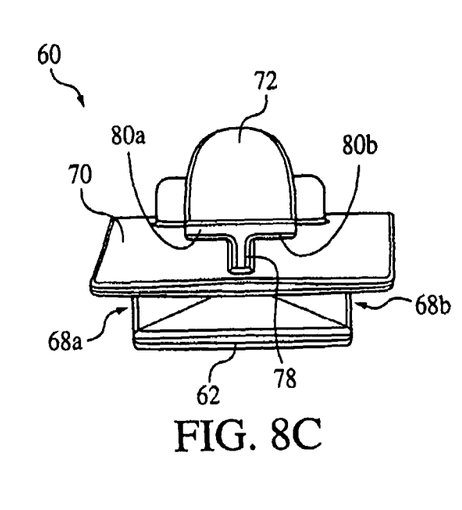

Forehead pad 30 attaches to a forehead support member 50 in a forehead support structure, generally indicated at 51 in a patient interface device. FIGS. 4-5C illustrate forehead support 30 attached to a forehead support member 50. More specifically, these figures show two separate forehead pads attached to two ends of forehead support member 50. It should be understood that the forehead support member shown in FIGS. 4-5C represents only one potential configuration for the forehead support member. In the embodiment, forehead support member 50 includes a first coupling portion 52 that slideably engages a second coupling member (not shown) that extends from the mask shell (also not shown). Of course, forehead pad 30 is also suitable for forehead support systems in which the forehead support member is not moveable relative to the remainder of the mask.

To allow the forehead pad to attach to forehead support member 50, forehead pad 30 includes an attachment member 54 coupled to first side 34 of base member 32. In the illustrated exemplary embodiment, attachment member 54 protrudes from first side 34 so that it can engage a cooperating element in the forehead support member. For example, the present invention contemplates providing a slot in the forehead support member serving as the receiving element for the attachment member. A stem portion 56 of attachment member inserts into the slot (not shown), and protrusions 58a and 58b extending from the stem cooperate with the inside surface of the slot to maintain the forehead pad in an engaged relation with the slot. This is perhaps best shown in FIG. 4. Furthermore, this slot and protrusion configuration allows the forehead pad to be removeably attached to the forehead support member simply by providing an open end to the slot or by deforming protrusions 58a and 58b during insertion of attachment member 54 into the slot and allowing them to return to their original shape following insertion.

It is to be understood that the attachment structure shown in FIGS. 1-5 represents only one possible configuration for attaching the forehead pad to the forehead support. Other configuration are contemplated by the present invention. For example, a slot can be provided in first side 34 of base member 32 and a protrusion provided in the forehead support member. In addition, or in the alternative, the ends of the base member can provide a surface or other attaching point.

The present invention also contemplates that the attachment member can be eliminated. In which case, the base member can be affixed to the base member using other techniques, such as by directly bonding the base member to the forehead support member via any conventional chemical process. The present invention also contemptates bonding the base member to a separate attachment structure to provide a more rigid attachment for the forehead support. The separate attachment structure can be formed form, a polycarbonate or other thermoplastic.

FIGS. 6-10C illustrates a second exemplary embodiment of a forehead pad 60 according to the principles of the present invention. Forehead pad 60 has a patient contacting member 62 and a neck portion 64 that are similar to the patient contacting member and neck portion of FIGS. 1-5C, including cutouts 66a and 66b. The primary difference between the second forehead pad embodiment of FIGS. 6-10C and the first embodiment of FIGS. 1-5C resides in the configuration of base member 70 and the use of two patient contacting members 62 with a common base member 70. As in the previous embodiment, the base member, patient contacting member, and neck portion are integrally formed from a common material, such as a low-durometer silicone or soft elastomer. This configuration allows a single part, i.e., forehead pad 60, to be attached to a forehead support member and provide two points of contact with the surface of the patient, i.e., at patient contacting members 62, rather than using two separate forehead pads, as shown, for example, in FIGS. 4-5C.

As in the previous embodiment, the patient contacting members are moveable relative to the base member 70 due to the cutouts 66a and 66b. In addition, cutouts 68a and 68b are provided on the sides of the neck portions to provide further degree of movement for the patient contacting members.

Figure 9:
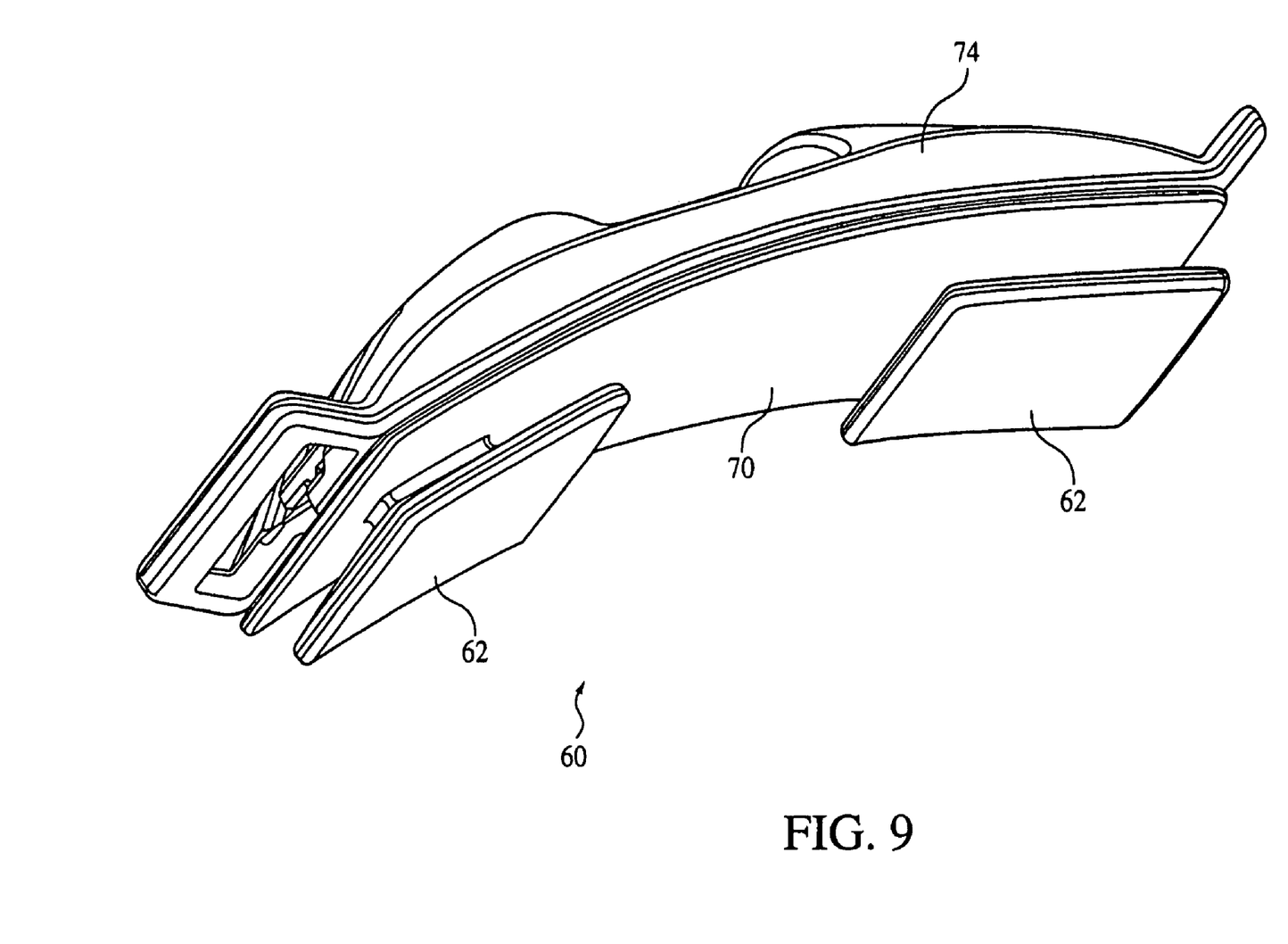
FIG. 9 is a top perspective view showing the forehead pad of FIG. 6 attached to a second embodiment of a forehead support member according to the principles of the present invention.
Figure 10A:
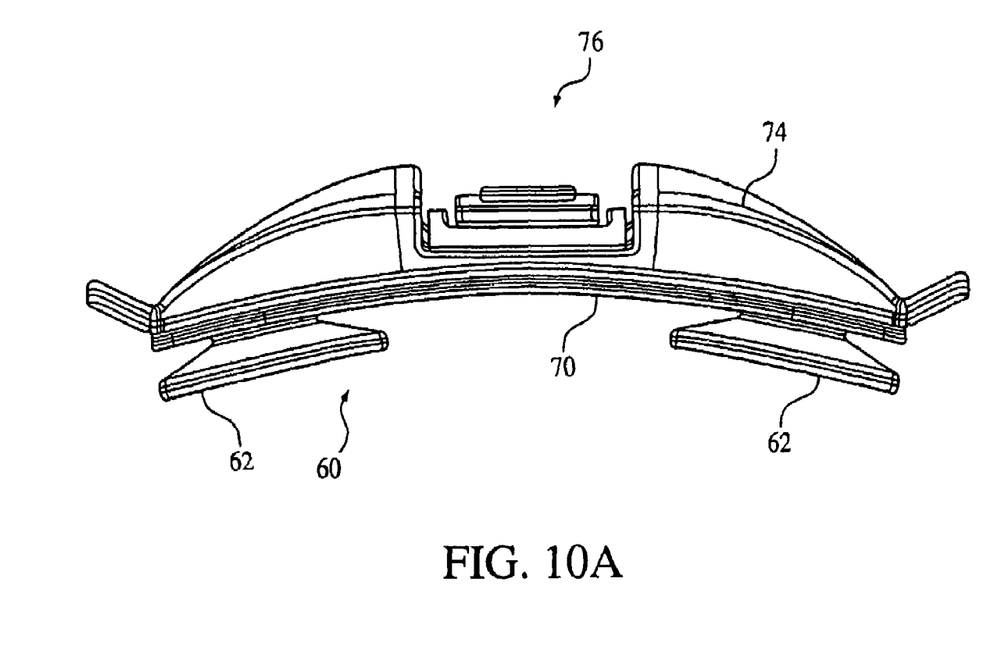
FIGS. 10A and 10B are top and side views, respectively, of the forehead pad and forehead support combination of FIG. 9.
Figure 10B:
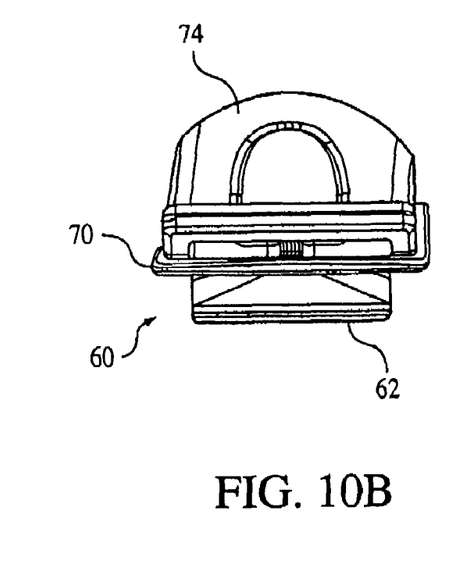

In the illustrated exemplary embodiment, a pair of attachment members 72 are provided for attaching forehead pad 60 to a forehead support member 74. FIGS. 9-10C show the attachment of forehead pad 60 to forehead support member 74. It should be noted that the forehead support member shown in FIGS. 9-10C is only a portion of the entire forehead support structure. For example, a support art (not shown) attaches to forehead support member at location 76 (see FIG. 10A). Attachment members 72, like those in the first embodiment, include a stem 78 and protrusions 80a and 80b extending from the stem to maintain the stem in engagement with a channel or slot in the forehead support member.

The present invention also contemplates providing further structures on the patient contacting portion of patient contacting member 38 and 62. For example, a fabric or other woven material can be disposed on surface 40 to enhance patient comfort and to allow any moisture that would otherwise be trapped between the surface of the patient and the surface of the patient contacting member to evaporate.

Figure 11:
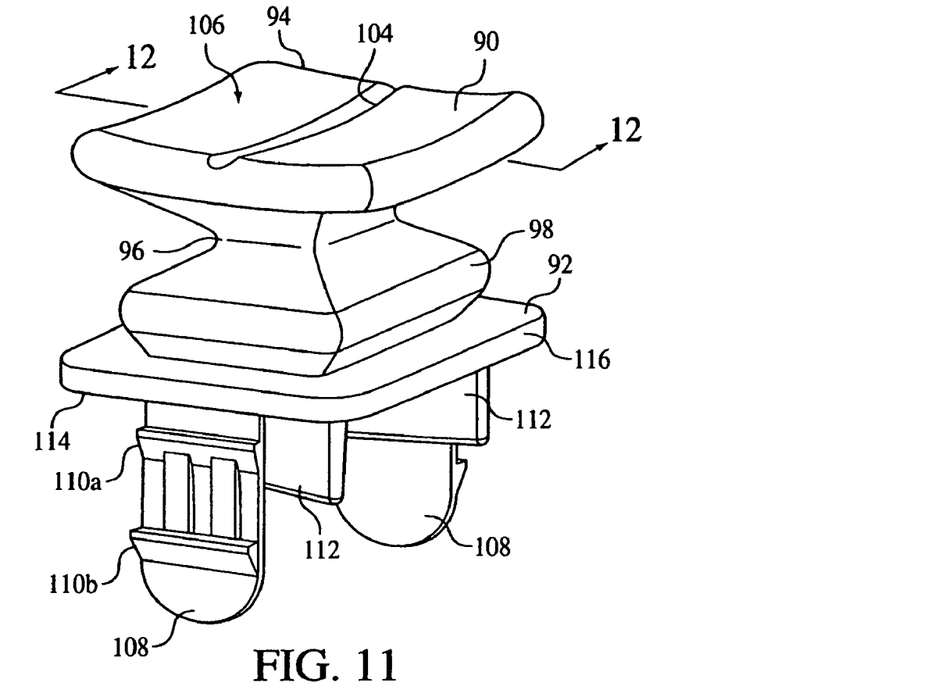
FIG. 11 is a top perspective view of a third embodiment of a forehead pad attached to a third embodiment of a forehead support according to the principles of the present invention.
Figure 12:
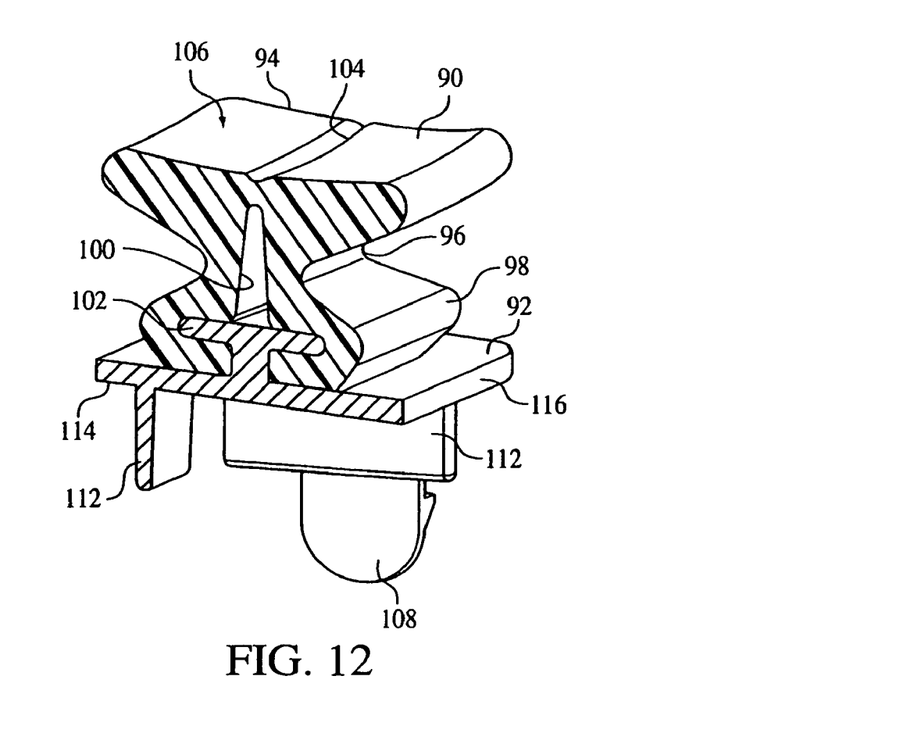
FIG. 12 is a cross-sectional view of the forehead pad and forehead support taken alone line 12-12 of FIG. 11.
Figure 13:
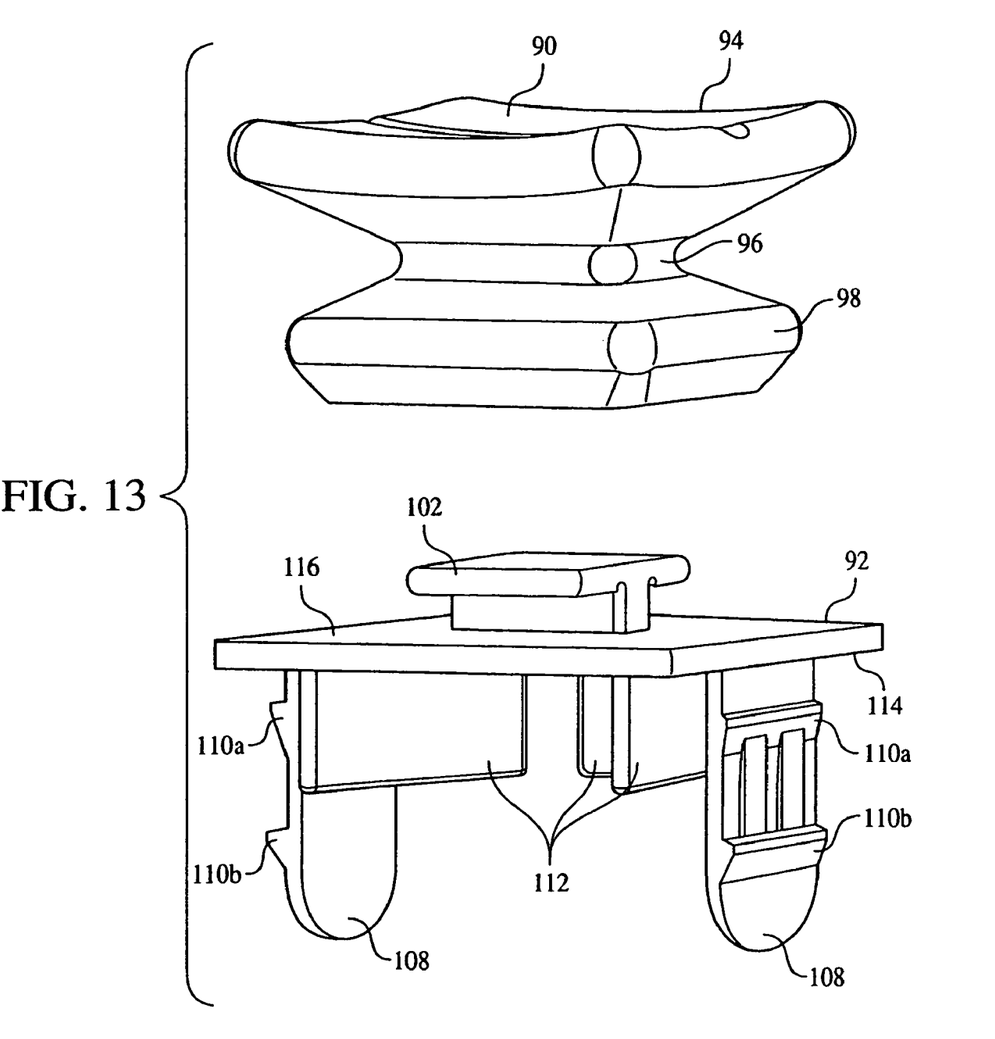
FIG. 13 is an exploded view of the forehead pad and forehead support of FIG. 11.

FIGS. 11-13 illustrate a third exemplary embodiment of a forehead pad 90 and a forehead support member 92 according to the principles of the present invention. Forehead pad 90 includes a patient contacting member 94, a neck portion 96, a base member 98, and cutouts on each side of the forehead pad, all of which are generally similar to those features shown in the forehead pad of FIGS. 1-5C. One difference between the third forehead pad embodiment of FIGS. 11-13 and the first embodiment of FIGS. 1-5C is that forehead pad 90 is more square-shaped than the first embodiment. Also, base member 98 does not include a protruding attachment member. Instead, the base member includes a slot 100 that receives a protruding member 102 provided on forehead support member 92 so that the forehead pad can be selectively attached to the forehead support. As in the previous embodiments, the base member, patient contacting member, and neck portion are preferably integrally formed from a common material, such as a low-durometer silicone or soft elastomer. Of course, the present invention also contemplates that these portions of the forehead pad, or combinations of these portions, can be formed separately from separate materials and joined using any conventional technique to form the overall forehead pad.

Another feature of forehead pad 90 not found in the previous embodiments is a groove 104 defined in a patient contacting surface 106 of patient contacting member 94. Groove 104 is provided to minimize or prevent the patient contacting surface from form a suction on the surface of the patient when the forehead pad contacts the user. Groove 104 also helps to vent air between patient contacting surface 106 and the user's skin. It is to be understood that the present invention contemplates that groove 106 can have other configurations, sizes (length/width/depth), and that more than one groove can be provided in the patient contacting member. These multiple groove can be intersecting or independent of one another on patient contacting surface 106.

Forehead support member 92 is configured to selectively lock onto a portion of a mask. To this end, the forehead support includes locking members 108 that fit into slots defined in the portion of the mask to which the forehead support attaches. An example, of a mask that includes a protrusion or tab extending from the mask shell over the patient's forehead to which a forehead support selectively attaches is described in U.S. Pat. No. 6,467,483 to Kopacko et al., the contents of which are incorporated herein by reference. Locking member 108 includes protrusions 110a and 110b that engage the sides of the slots to maintain the forehead support in contact with the mask.

In the illustrated embodiment, a plurality of alignment tabs 112 are also provide on forehead support. These tabs allow the distance between the forehead pad and the forehead attachment portion of the mask to which the forehead pad attach, to be controlled. When the forehead support is disposed in a first orientation relative to the forehead attachment portion of the mask, alignment tabs 112 fit into slots defined in the forehead attachment portion of the mask so that a surface 114 of a base portion 116 is generally adjacent a surface of the forehead attachment portion of the mask. In this orientation, locking tab 110a fix the locking member to the forehead attachment portion of the mask. When the forehead support is disposed in a second orientation relative to the forehead attachment portion of the mask, for example by being rotated 180°, alignment tabs 112 do not fit into the slots defined in the forehead attachment portion of the mask, but instead butt against the surface of the forehead attachment portion of the mask. In this orientation, locking tabs 110b fix the locking member to the forehead attachment portion of the mask. The Comfort Classic mask manufactured by Respironics, Inc. of Murrysville, Pa., is an example of a mask having a forehead spacer in the distance between the pad and the mask can be controlled in the manner described above.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A forehead pad comprising:
   a base member having a first side adapted to be coupled to a forehead support member and a second side;
   a first patient contacting member having a first side adapted to contact a surface of a patient and a second side; and
   a generally rectangular first neck portion coupled to the second side of the base member and the second side of the first patient contacting member, wherein the first neck portion has a longitudinal axis along a length of the rectangular first neck portion and includes a plurality of cutouts disposed around the periphery of the first neck portion and defined in a side of the first neck portion generally parallel to the longitudinal axis so as to allow at least a portion of the first patient contacting member to move relative to the base member in a direction generally perpendicular to the longitudinal axis responsive to a force being applied to the first patient contacting member, and wherein the base member, the first patient contacting member, and the first neck portion are integrally formed from a common material to define a unitary structure.

2. The forehead pad of claim 1, wherein the first neck portion includes two cutout portions provided on opposing sides of the forehead support to allow the first patient contacting member to move in one-dimension relative to the base member.

3. The forehead pad of claim 1, wherein the common material is a low-durometer silicone or soft elastomer.

4. The forehead pad of claim 1, wherein the first side of the first patient contacting member is relatively planar.

5. The forehead pad of claim 1, wherein the cutout in the neck portion is sized and configured such that an angle of approximately 30 degrees is defined between the second side of the base member and the second side of the first patient contacting member.

6. The forehead pad of claim 1, further comprising an attachment member coupled to the first side of the base member.

7. The forehead pad of claim 1, further comprising:
   a second patient contacting member having a first side adapted to contact a surface of a patient and a second side; and
   a second neck portion coupled to the second side of the base member and the second side of the second patient contacting member, wherein the second neck portion includes at least one cutout to allow at least a portion of the second patient contacting member to move relative to the base member.

8. The forehead pad of claim 7, further comprising an attachment member coupled to the first side of the base member.

9. The forehead pad of claim 1, wherein the first neck portion includes four cutout portions with each of the four cutout portions being provided on one side of the forehead pad to allow the first patient contacting member to move in two-dimensions relative to the base member.

10. A forehead support comprising:
    a forehead support member; and
    a forehead pad adapted to be coupled to the forehead support member, wherein the forehead pad comprises:
    a base member having a first side adapted to be coupled to a forehead support member and a second side;
    a first patient contacting member having a first side adapted to contact a surface of a patient and a second side; and
    a generally rectangular first neck portion coupled to the second side of the base member and the second side of the first patient contacting member, wherein the first neck portion has a longitudinal axis along a length of the rectangular first neck portion and includes a plurality of cutouts disposed around the periphery of the first neck portion, wherein the cutouts defined in a side of the first neck portion generally parallel to the longitudinal axis so as to allow at least a portion of the first patient contacting member to move relative to the base member in a direction generally perpendicular to the longitudinal axis responsive to a force being applied to the first patient contacting member, and wherein the base member, the first patient contacting member, and the first neck portion are integrally formed from a common material to define a unitary structure.

11. The forehead support of claim 10, wherein the first neck portion includes two cutout portions provided on opposing sides of the forehead support to allow the first patient contacting member to move in one-dimension relative to the base member.

12. The forehead support of claim 10, wherein the common material is a low-durometer silicone or soft elastomer.

13. The forehead support of claim 10, wherein the first side of the first patient contacting member is relatively planar.

14. The forehead support of claim 10, wherein the cutout in the neck portion is sized and configured such that an angle of approximately 30 degrees is defined between the second side of the base member and the second side of the first patient contacting member.

15. The forehead support of claim 10, wherein the forehead pad further comprises an attachment member coupled to the first side of the base member.

16. The forehead support of claim 10, wherein the forehead pad further comprises:
    a second patient contacting member having a first side adapted to contact a surface of a patient and a second side; and
    a second neck portion coupled to the second side of the base member and the second side of the second patient contacting member, wherein the second neck portion includes at least one cutout to allow at least a portion of the second patient contacting member to move relative to the base member.

17. The forehead pad of claim 16, further comprising an attachment member coupled to the first side of the base member.

18. The forehead pad of claim 10, wherein the first neck portion includes four cutout portions with each of the four cutout portions being provided on one side of the forehead pad to allow the first patient contacting member to move in two-dimensions relative to the base member.

* * * * *